(12) United States Patent
Bruder et al.

(10) Patent No.: US 7,835,485 B2
(45) Date of Patent: Nov. 16, 2010

(54) METHOD FOR SCATTERED RADIATION CORRECTION IN X-RAY IMAGING DEVICES

(75) Inventors: Herbert Bruder, Höchstadt (DE);
Martin Petersilka, Adelsdorf (DE);
Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 261 days.

(21) Appl. No.: 12/076,040

(22) Filed: Mar. 13, 2008

(65) Prior Publication Data
US 2008/0240340 A1 Oct. 2, 2008

(30) Foreign Application Priority Data
Mar. 28, 2007 (DE) .................. 10 2007 014 829 U

(51) Int. Cl.
*A61B 6/00* (2006.01)
(52) U.S. Cl. .............................. 378/7; 378/86
(58) Field of Classification Search ..................... 378/7, 378/9
See application file for complete search history.

(56) References Cited

U.S. PATENT DOCUMENTS

| 6,980,626 | B2 | 12/2005 | Groh et al. | |
|---|---|---|---|---|
| 2002/0048339 | A1* | 4/2002 | Schneider et al. | 378/7 |
| 2004/0079232 | A1* | 4/2004 | Groh et al. | 96/1 |
| 2004/0114710 | A1* | 6/2004 | Ozaki | 378/9 |
| 2004/0202360 | A1* | 10/2004 | Besson | 382/131 |
| 2007/0025498 | A1* | 2/2007 | Matsuda | 378/9 |
| 2007/0086561 | A1 | 4/2007 | Bruder et al. | |
| 2007/0140416 | A1* | 6/2007 | Nukui | 378/19 |
| 2007/0253524 | A1 | 11/2007 | Bruder et al. | |

FOREIGN PATENT DOCUMENTS

| DE | 10232429 | 1/2004 |
|---|---|---|
| DE | 102005048397 | 4/2007 |
| DE | 102006019923 | 11/2007 |

* cited by examiner

*Primary Examiner*—Edward J Glick
*Assistant Examiner*—Alexander H Taningco
(74) *Attorney, Agent, or Firm*—Harness, Dickey & Pierce, P.L.C.

(57) ABSTRACT

A method is disclosed for scattered radiation correction in x-ray imaging devices having a number of x-ray sources that can be moved around an examination object in at least one scanning plane during a measurement pass. During the measurement pass, a number of x-ray projections are recorded at different projection angles with simultaneous use of the x-ray sources. In at least one embodiment of the present method, parameters characterizing an outer object contour are determined in the scanning plane from measured data of different x-ray projections. In at least one embodiment, on the basis of one object contour section whose characterizing parameters have been determined from x-ray projections that lie in front of and/or behind the respective x-ray projection by a defined projection angle range, for each x-ray projection an assigned scattered radiation distribution is then retrieved or is interpolated in a database from scattered radiation distributions for object contour sections with similar characterizing parameters. This scattered radiation distribution is then used for the correction of the measured data for the respective x-ray projection. In at least one embodiment, the method enables scattered radiation correction in conjunction with operation of the x-ray sources.

16 Claims, 3 Drawing Sheets

METHOD FOR SCATTERED RADIATION CORRECTION IN X-RAY IMAGING DEVICES

PRIORITY STATEMENT

The present application hereby claims priority under 35 U.S.C. §119 on German patent application number DE 10 2007 014 829.3 filed Mar. 28, 2007, the entire contents of which is hereby incorporated herein by reference.

FIELD

Embodiments of the invention generally relate to a method for scattered radiation correction in x-ray imaging devices. For example, the may relate to methods for scattered radiation correction in x-ray imaging devices having a number of x-ray sources that can be moved around an examination object in at least one scanning plane during a measurement pass, in the case of which during the measurement pass a number of x-ray projections are recorded at different projection angles with simultaneous use of the x-ray sources.

BACKGROUND

In x-ray imaging, an examination object is trans-irradiated in at least one direction by x-radiation, and the intensity of the x-radiation impinging on an x-ray detector opposite the x-ray source is measured. The measured intensity I is a function of the absorption properties of the trans-irradiated material, and of the path of the x-ray through the trans-irradiated object. In accordance with the law of absorption, the measured intensity I depends in this case exponentially on the irradiated intensity $I_0$, in which case it holds that $I/I_0 = e^{-\mu(x)dx}$. As a rule, in x-ray imaging the signal processing is performed by digitization and logarithmation of the measured signals such that the attenuation value distribution $\mu(y,z)$ or $\mu(x,y,z)$ of the examination object can be obtained. Logarithmated signals are also used in computer aided tomography (CT).

A fundamental problem in x-ray imaging is represented by scattered radiation, which leads to a reduction in the image contrast, in particular to a undesired brightness fog over the entire image. In the case of imaging x-ray devices having one x-ray source, use is made upstream of the detector of so-called scattered beam collimators that uncover upstream of each detector element only the direct radiation direction between the detector element and focus of the x-ray source, and largely shade all other directions. It is possible in this way for a large fraction of the scattered radiation that is produced by transverse scattering of the x-rays at the volume elements of the examination object not to reach as far as the detector elements.

Even in the case of x-ray imaging devices having a number of x-ray sources, so called two- or multifocussed/detector systems, use is made of such scattered beam collimators upstream of the detector elements. In any case, in these systems scattered beam collimators cannot reduce the scattered radiation that is produced by beams from an x-ray source arranged at an angular offset and which has the same spatial orientation as the direct x-ray beam from the x-ray source opposite the detector. This undesired scattered radiation leads to corruption of the measured data and thus to image artifacts.

DE 102 32 429 B3 discloses a method for scattered radiation corruption in an x-ray imaging device having two x-ray sources and two x-ray detectors. In the method of this publication, the two x-ray sources arranged at an angular offset from one another are operated at least temporarily in an alternating fashion in order to measure directly in the image system composed of x-ray source and x-ray detector, which image system in each case is not switched on, the scattered radiation actually occurring that originates from the x-ray source in operation in the second image system.

Measured data of the respective image systems can then be corrected on the basis of the respectively measured scattered radiation distribution. However, carrying out this method requires the x-ray sources to be operated at least partially in alternating fashion, and so at these times image information from the measurement pass is lacking, at least in the detector of the image system that is not being operated. These gaps in the data acquisition are disturbing, particularly in the case of CT cardio pictures, which require a high temporal resolution.

SUMMARY

In at least one embodiment of the present invention, a method is disclosed for scattered radiation correction in x-ray imaging devices having a number of x-ray sources that enables the scattered radiation to be corrected during simultaneous operation of the x-ray sources without loss of image information. Furthermore, in at least one embodiment, an x-ray imaging system is provided that enables such a scattered radiation correction.

In the case of at least one embodiment of the proposed method for scattered radiation correction in x-ray imaging devices having a number of x-ray sources that can be moved around an examination object in at least one scanning plane during a measurement pass, during the measurement pass a number of x-ray projections are recorded at different projection angles with simultaneous use of the x-ray sources. Parameters characterizing an outer object contour are determined in the scanning plane from measured data of different x-ray projections, that is to say at different projection angles.

On the basis of at least one object contour section whose characterizing parameters have been determined from x-ray projections that lie in front of and/or behind the respective x-ray projection by a defined projection angle range, for each x-ray projection an assigned scattered radiation distribution is then retrieved in a database or is interpolated from scattered radiation distributions for object contour sections with similar characterizing parameters. The correction of the measured data of the respective x-ray projections is then carried out with the aid of this scattered radiation distribution.

The proposed method of at least one embodiment is based on the finding that during simultaneous operation of a number of angularly offset x-ray sources arranged around the examination object the scattered radiation passing from an x-ray source into the detector assigned to the other x-ray source is substantially determined by the shape of the scattering edge. The scattering edge is in this case the outer object contour of the examination object. Furthermore, use is made of the fact that characterizing parameters of this object contour can be determined from the measured data or the different x-ray projections.

In at least one embodiment, an important role is played by an x-ray projection to be corrected only by the section of the object contour on which the x-radiation of the x-ray source not belonging to this x-ray projection impinges at this instant, and that causes a scattering in relation to the x-ray detector belonging to the x-ray projection, without passage through the object. This section of the object contour therefore relates respectively to the side of the object facing the x-ray detector of the respective x-ray projection. This is a single object contour section in the case of an x-ray device having two x-ray sources. In the case of an x-ray device having more than two x-ray sources, it can also be a number of object contour sections. The position of these object contour sections with reference to the projection angles is known to the person skilled in the art from the geometrical arrangement of the x-ray device and the x-ray tubes arranged thereon. Since, in the case of such an x-ray device, a measurement pass is performed by a movement of the x-ray sources around the examination object, generally on a circle or partial circle, it is possible to specify an angle range of the projections in front of and/or behind the x-ray projection currently being considered, that is to say to be corrected, from whose associated x-ray projections the parameters characterizing the respective section of the object contour are determined.

In order to correct the respective x-ray projection, a search is then made, in a database provided, for an object contour section having characterizing parameters that are the same or come closest, and the scattered radiation distribution assigned in the database to this object contour section is retrieved. Here, it is also possible to use an interpolation method in order to interpolate the scattered radiation distribution for the object contour section being sought from scattered radiation distributions of two object contour sections that come closest to the object contour section being sought. Of course, in this case the method requires the provision of a database having a multiplicity of object contour sections and/or characterizing parameters of object contour sections such as are determined with the aid of the method, as well as associated scattered radiation distributions. In this case, of course, the data of the database are adapted to the x-ray device being used. This relates first and foremost to the mutual arrangement of the x-ray sources and x-ray detectors.

The scattered radiation distribution in this case preferably includes intensity values of the scattered radiation $I_{str}$ for each detector element or for each continuous region of the detector elements of the x-ray detector, the database preferably being designed as look-up table (LUT). The database also preferably includes the information relating to the output intensity $I_0$ of the x-ray sources for which this intensity of the scattered radiation $I_{str}$ holds. In the case of an intensity of the x-ray sources that deviates therefrom, an appropriate linear scaling of the retrieved scattered radiation intensities is then performed during the respective measurement pass. The output intensity can also be characterized by the x-ray current in the case of x-ray devices having x-ray tubes.

An x-ray projection is understood in the present patent application as an x-ray image recording at a defined projection angle in the case of which an x-ray beam, expanded in a fan-shape fashion, emanating from the x-ray source strikes the x-ray detector. Different x-ray projections within the meaning of the present patent application differ in the projection angle.

At least one embodiment of the present invention is applied chiefly in computed tomography. The several x-ray sources can in this case be formed by a number of x-ray tubes arranged on the rotary frame of the computer tomograph, an x-ray detector respectively lying on the rotary frame opposite each x-ray tube. The method of at least one embodiment can, however, also be used with computer tomographs of different design that, for example, have a stationary detector ring, or in the case of which no mechanically movable components are used. Such computer tomographs are also known as 4th and 5th generation computer tomographs. Furthermore, the method of at least one embodiment can also be used in the case of so-called C-arc systems in which the x-ray sources generally carry out only a partial revolution of $\geq 180°$ around the examination object.

The characterization of the object contour is preferably performed in at least one embodiment of the present method by determining a number of object tangents for the measured data of the different x-ray projections. The object contour in a specific section is largely defined when the position of a few, for example three, object tangents is known. The object tangents can, in turn, be determined straight away from the measured data from different x-ray projections.

By determining the measurement channel or the detector element from which a specific object attenuation is exceeded for the first time starting from the outer measurement channels, it is possible to determine the spatial position of an object tangent on the respective side of the object from the known projection angle and relative position between the detector element or measurement channel and the x-ray source or the x-ray focus. If this is carried out for a further two x-ray projections that differ from one another by a specific projection angle, then three object tangents that characterize the object contour on this side are available for the corresponding side of the object. The object tangents, defined by their spatial position, can already be used in this case as characteristic parameters of this section of the object contour that enable the associated scattered radiation distribution to be retrieved from the database. In this case, the respective object contour section is then likewise characterized by three object tangents in the database. Alternatively, the characterization can also be performed on the basis of one tangent and the difference between this tangent and the other two tangents. The entries in the database are then also adapted here correspondingly.

Other features can also be used for characterizing the object contour or the respective section of the object contour. Examples of this are derivations of the tangent in accordance with the projection angle, or the increase in the attenuation with the fan angle of the x-ray beam when the beam moves into the object. For example, the increase in the x-ray attenuation in small angular steps of 2° could be used for characterization by determining a functional relationship of a value X and the angle in accordance with the following formula: X (angle)=attenuation (tangential beam)−attenuation (tangential beam+angle).

At least one embodiment of the method requires the prior provision of the database with the entries for different characteristics of object contour sections and the associated scattered radiation distributions. These database entries or tables can be determined in advance in various ways. Thus, it is possible in one refinement to make a prior measurement of the scattered radiation distribution and the projection shadows for a multiplicity of differently shaped phantoms. The characterizing variables for the respective object contour section can be determined in each case for all projection angles from each such measurement. The measured scattered radiation distribution is then incremented to the table entry corresponding to these characterizing variables. This must be carried out for sufficiently numerous phantoms and positionings so that all possible parameter combinations occur and the table is filled. Upon conclusion, the number of the scattered radiation vectors incremented in each table entry is used for division such that averaging results. Gaps in the table can also be filled by interpolation.

A further possibility for drawing up the table resides in undertaking to simulate the scattered radiation distribution for example with the aid of the known Monte Carlo method for selected phantom constellations in order to fill the table.

Furthermore, the scattered radiation distribution can also be calculated, for example, from analytical models that are based on primary beam intensities, differential effective cross sections and absorption lengths. Here, the radiation intensity is calculated from the primary radiation (scattered radiation)

striking the scattering location, and the angular relationships of scattering beam, object tangent and measurement beam.

At least one embodiment of the proposed method thus enables scattered radiation correction in x-ray imaging devices having a number of x-ray sources that can be moved around an examination object in at least one scanning plane during a measurement pass with simultaneous operation of the x-ray sources. By determining features, characterizing sections of the object contour, from the measured data occurring during the measurement pass, a relatively accurate determination of the scattering situation, and thus a correction of the scattered radiation, can be performed in conjunction with the database provided. Here, the correction tables can originate from prior measurements on different phantoms such that a very accurate determination of the scattered radiation is possible. Additional hardware is not required for carrying out at least one embodiment of the method. The correction can also be carried out with a low outlay on computing time owing to the use of a database or a suitable table.

The x-ray imaging system designed for carrying out at least one embodiment of the method is known to include a number of x-ray sources that can be arranged so as to move around an examination volume, and one or more x-ray detectors. The x-ray imaging system can in this case be a computer tomograph or else a C-arc x-ray device.

The signal processing device of the x-ray imaging system for processing the measurement signals that are supplied during the trans-irradiation of an examination object by the one or more x-ray detectors comprises in the case of the proposed x-ray imaging system at least one processing module that carries out the scattered radiation correction in accordance with at least one embodiment of the proposed method. This processing module is preferably designed as a computer program with the aid of a corresponding computer program code. Furthermore, the signal processing device must include a storage unit, or be connected to such a storage unit, on which the database with the characteristics of the object contours and associated scattered radiation distributions is set up.

BRIEF DESCRIPTION OF THE DRAWINGS

The proposed method is explained in more detail once more below with the aid of an example embodiment in conjunction with the drawings, in which.

DETAILED DESCRIPTION OF THE EXAMPLE EMBODIMENTS

Figure 1:
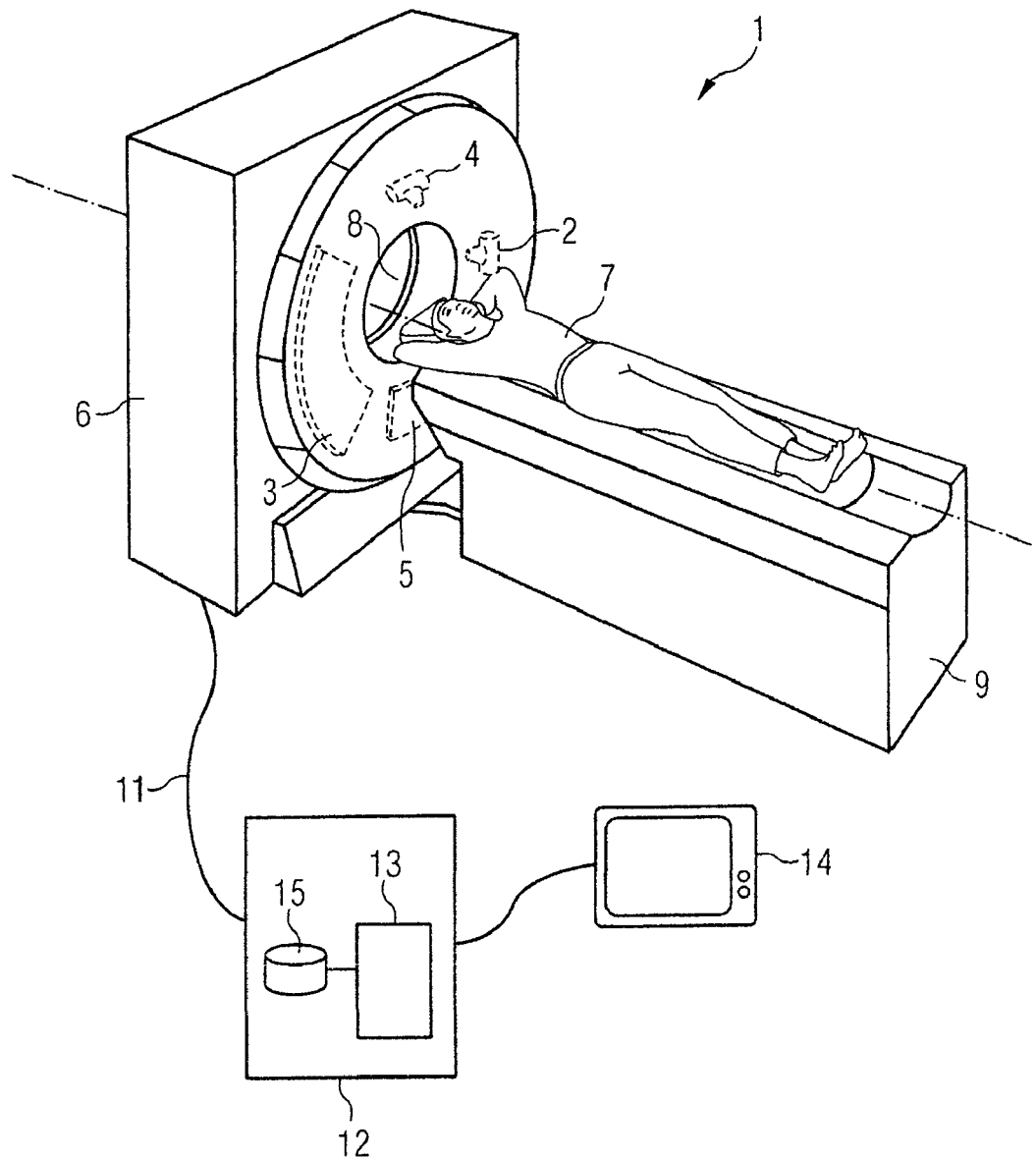
FIG. 1 shows example of an x-ray imaging system designed for carrying out an embodiment of the method.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a schematic of a computer tomograph 1 that is designed for carrying out an embodiment of the proposed method. The computer tomograph 1 has a scanning system 6 that includes a rotary frame having two x-ray tubes 2, 4 fastened thereon, and two x-ray detectors 3, 5 opposite the x-ray tubes. In this example, the two x-ray tubes 2, 4 are arranged on the rotary frame in a fashion offset by 90° from one another. Provided between the x-ray tubes 2, 4 and the x-ray detectors 3, 5 is an opening 8 into which a patient 7 can be pushed on a movable patient couch 9 along the system axis 10 and be scanned in the process. The control of the computer tomograph is performed by an control and computing unit 12 that in this example also carries out the signal processing of the measurement signals obtained by the detectors 3, 5. The control and computing unit 12 is connected via a control and data line 11 to the scanning system 6, and also controls the feed of the patient couch 9.

The measured data recorded with the detectors 3, 5 during a measurement pass as the patient 7 is being scanned are led via the control and data line 11 to the computing unit 12 and reconstructed with the aid of suitable digital programs such that it is possible to output on a monitor 14 a tomograph image representation or volume representation of a region of interest of the patient 7. The computing unit 12 includes, in the case of an embodiment of the present invention an additional processing module 13 that reprocesses the measured data before the image reconstruction for the purpose of carrying out the scattered radiation correction. Here, the retrieved scattered radiation intensities are subtracted from the measured intensities. The processing module operates in this case in accordance with the proposed method, as is explained, for example, in the following sections of the description. The processing module 13 in this case has access to a storage unit 15 in which the table with the scattered radiation distributions is stored.

During a measurement pass, that is to say during a rotation of the rotary frame with the x-ray tubes 2, 4 and x-ray detectors 3, 5 around the patient 7, two x-ray tubes are operated simultaneously in the present method such that measured data and/or recorded are supplied simultaneously with the two image systems. This reduces the time required for recording a layer or volume image. On the other hand, during the simultaneous operation of the two x-ray tubes an increased scattered radiation fraction reaches the respective detectors. This scattered radiation fraction is caused in each case by the x-ray tubes not belonging to the detector.

Figure 2:
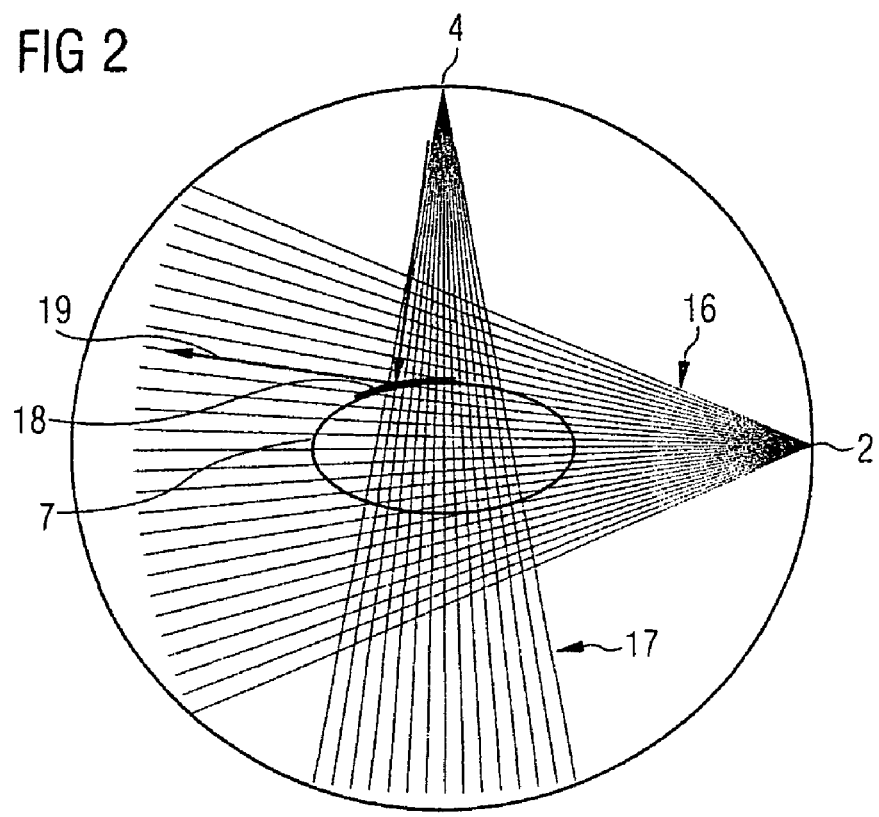
FIG. 2 shows a schematic for illustrating the scattering in the case of an embodiment of an x-ray imaging system.

Scattering is substantially defined by the shape of the scattering edge, that is to say the outer object contour. This is illustrated in the snapshot of FIG. 2, which shows the x-ray beams 16 and 17, widened in a fan-shaped fashion, emanating at this instant from the two x-ray sources 2, 4, respectively, which beams penetrate the patient 7. It is indicated in this figure that, owing to scattering at a section 18 of the object contour, a portion of the x-radiation of the x-ray source 4 strikes the x-ray detector of the other x-ray source 2 from the same direction and falsifies the measurement signal there (scattered radiation 19). The shape of this section 18 of the object contour in this case determines the height of the fraction of scattered radiation in the respective detector elements or measurement channels of the detector of the x-ray source 2.

Figure 3:
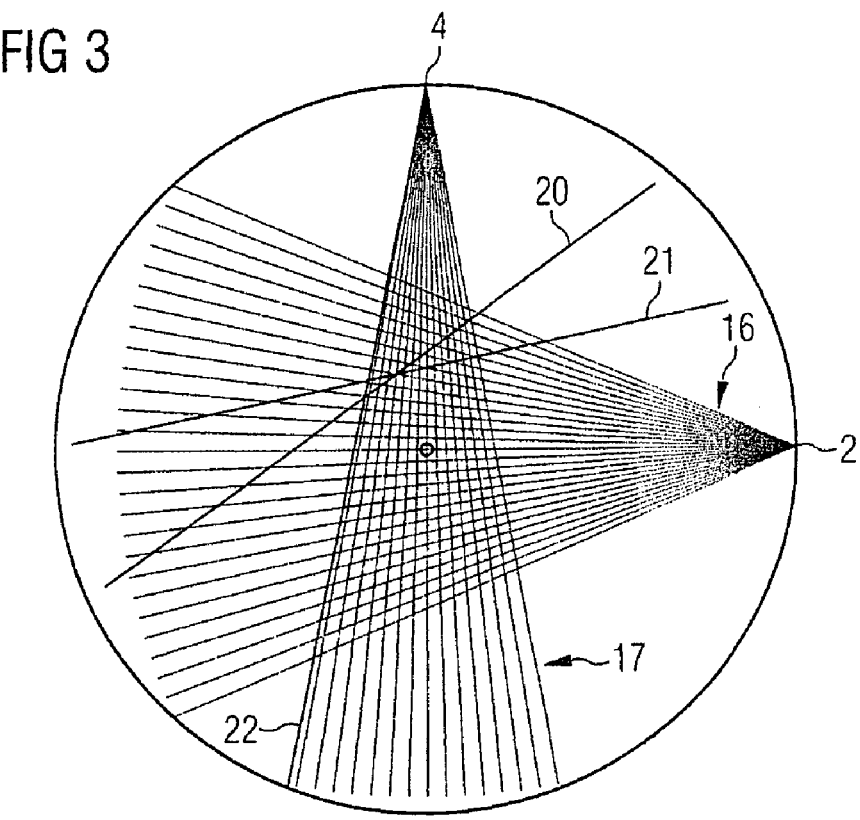
FIG. 3 shows an example of the characterization of the object contour by object tangents.

In the case of an embodiment of the proposed method, this object contour is now characterized in the respective section by the position of a number of object tangents. To this end, FIG. 3 shows an example of three object tangents 20, 21, 22 that characterize a corresponding section of the object contour.

These object tangents are determined by prescribing a threshold value for the object attenuation of the x-radiation. For example, starting from the outer measurement channels of the x-ray detector, it would be possible to determine the measurement channel in the case of which the object attenuation reaches the threshold value of ½. In the case of a projection where the fan of the x-ray beam detects the entire object, two boundaries of the object in the scanning plane are detected via this threshold value. The associated measurement channels or detector elements of the detector, in the case of which the corresponding object attenuation is reached, are determined. The object tangents at this point on both sides of the object can therefore be determined from the known position of these measurement channels or detector elements in relation to the x-ray source. In turn, the object tangents lying at another point are determined in the case of variation of the projection angle, that is to say using the measured data from another projection.

The position of the object tangents determined in this way in a specific angular range of the projections is used for characterizing object contour in this section. In the present example, with a 90° angular offset of the two x-ray sources, this is carried out in an angular range between 0° and 90° before the considered projection of one x-ray tube 2 for which this characterization is used to correct the scattered radiation. The object tangents are denoted below by $b_1, b_2 \ldots b_n$.

In this example, an N-dimensional table containing vectors of scattered radiation intensities as a function of $b_k$ is provided for an embodiment of the method. The associated scattered radiation intensities are calculated or measured in advance for different object contours in the case of such a configuration of the x-ray imaging system, as has already been explained above in the description. For the purpose of correcting the scattered radiation of a projection, a look-up is then made in this N-dimensional table in order to obtain the scattered radiation distribution for the object tangents determined in relation to this x-ray projection. This scattered radiation intensity is then subtracted from the signal of the considered projection, if appropriate after scaling in accordance with the prevailing tube current conditions.

This can be performed, for example, by digitization and logarithmation of the measurement signals t of the detector, there subsequently being subtracted from the logarithmated measurement signal $\ln(t)$ correction values that are obtained from a series expansion of the logarithm $\ln(1-s/t)$. The series expansion is truncated here after the first order, at the earliest. In this case, the variable s is the scattered radiation signal, obtained from the table, for the corresponding measurement channel or the corresponding detector element.

Figure 4:
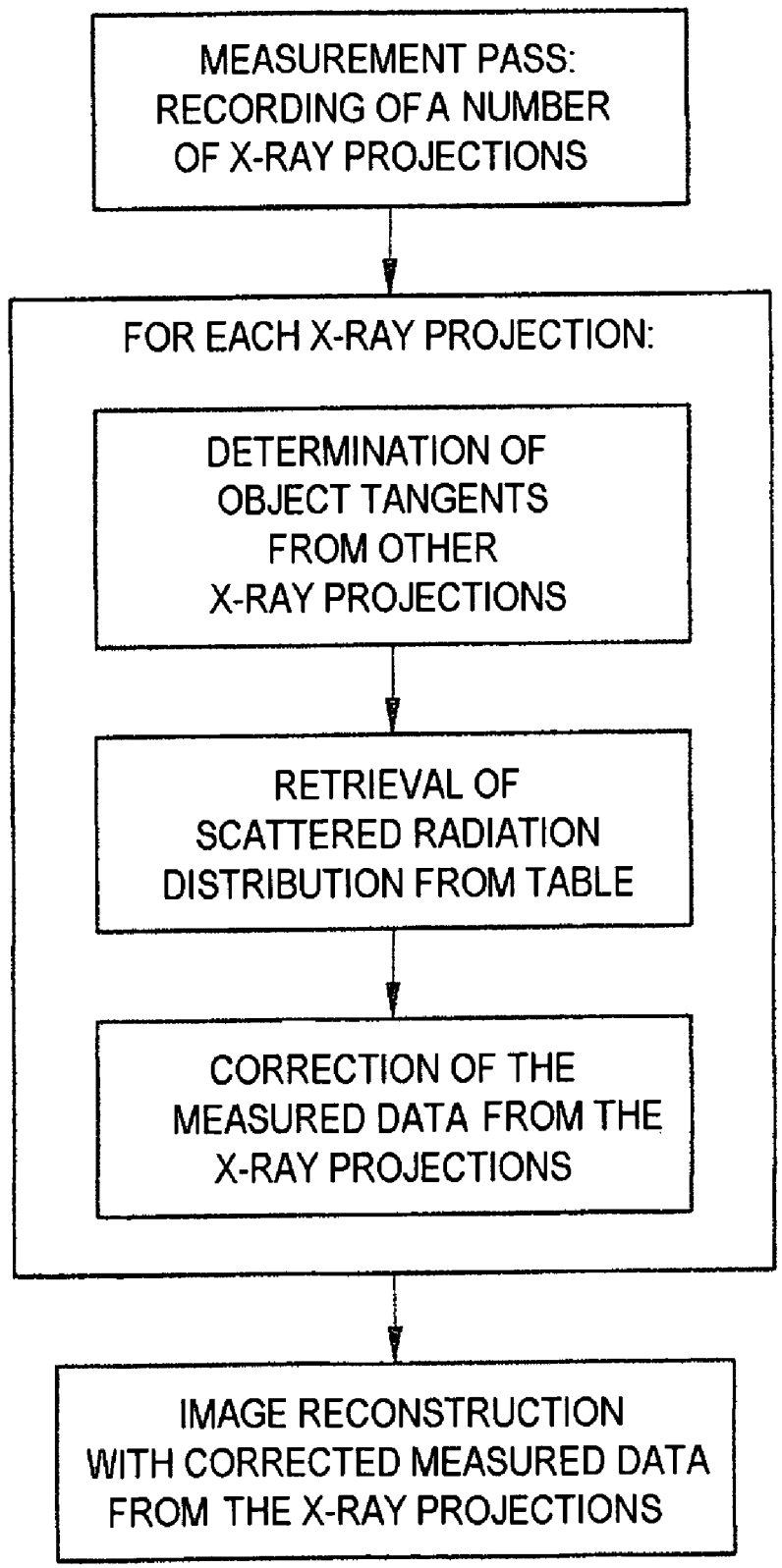
FIG. 4 shows a schematic overview of the method sequence in the case of an embodiment of the proposed method.

The correction of the projections of the other x-ray tube 4 is performed in the same way. In the present example, use is preferably made of the x-ray projections of the x-ray tube 2 for the purpose of determining the object tangents, since said x-ray tube has in this example a (larger) fan angle by means of which the object is scanned completely with each projection (compare FIG. 2). FIG. 4 is an overview of the method steps of an embodiment of the proposed method.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for scattered radiation correction in x-ray imaging devices including a number of x-ray sources, movable around an examination object in at least one scanning plane during a measurement pass, the method comprising:
   recording, during the measurement pass, a number of x-ray projections at different projection angles with simultaneous use of the x-ray sources;
   determining parameters, characterizing an outer object contour in a scanning plane, from measured data of different x-ray projections;
   at least one of retrieving, by a signal processing device, an assigned scattered radiation distribution from a database and interpolating, by a signal processing device, a scattered radiation distribution from scattered radiation distributions for object contour sections with similar characterizing parameters, for each x-ray projection, on the basis of at least one object contour section whose characterizing parameters are determined from x-ray projections that lie at least one of in front of and behind the respective x-ray projection by a defined projection angle range; and
   using, by a signal processing device, the at least one of retrieved and interpolated scattered radiation distribution for correction of the measured data of a respective x-ray projection.

2. The method as claimed in claim 1, wherein a number of object tangents are determined as characterizing parameters of the outer object contour from the measured data of the different x-ray projections.

3. The method as claimed in claim 2, wherein each object tangent is determined by determining a measurement channel in the respective x-ray projection, a prescribable threshold value of the radiographic attenuation being reached starting from outer measurement channels.

4. The method as claimed in claim 3, wherein the scattered radiation distribution is at least one of retrieved and interpolated at least one of on the basis of the object tangents determined from x-ray projections that lie at least one of in front of and behind the respective x-ray projection by the defined projection angle range, and on the basis of variables derived therefrom.

5. The method as claimed in claim 2, wherein the scattered radiation distribution is at least one of retrieved and interpolated at least one of on the basis of the object tangents determined from x-ray projections that lie at least one of in front of and behind the respective x-ray projection by the defined projection angle range, and on the basis of variables derived therefrom.

6. The method as claimed in claim 2, wherein the at least one of retrieved and interpolated scattered radiation distributions are scaled for the correction of the measured data on the basis of an intensity of the x-radiation emitted by the x-ray sources during the measurement pass.

7. The method as claimed in claim 2, wherein the scattered radiation distributions are retrieved from a table.

8. The method as claimed in claim 2, wherein the defined projection angle range at least one of in front and behind the respective x-ray projection is selected as a function of the mutual position of the x-ray sources within the range of $0°$ and $90°$.

9. The method as claimed in claim 2, wherein the method is for scattered radiation correction in a computer tomograph with a number of x-ray sources.

10. The method as claimed in claim 1, wherein the at least one of retrieved and interpolated scattered radiation distributions are scaled for the correction of the measured data on the basis of an intensity of the x-radiation emitted by the x-ray sources during the measurement pass.

11. The method as claimed in claim 1, wherein the scattered radiation distributions are retrieved from a table.

12. The method as claimed in claim 1, wherein the defined projection angle range at least one of in front and behind the respective x-ray projection is selected as a function of the mutual position of the x-ray sources within the range of $0°$ and $90°$.

13. The method as claimed in claim 1, wherein the method is for scattered radiation correction in a computer tomograph with a number of x-ray sources.

14. An x-ray imaging system, comprising:
   a plurality of x-ray sources, movable around an examination object in at least one scanning plane during a measurement pass;
   at least one x-ray detector to record, during the measurement pass, a number of x-ray projections at different projection angles with simultaneous use of the x-ray sources; and
   a signal processing device to process measurement signals that are supplied by the at least one x-ray detector during the transit radiation of the examination object, the signal processing device including a processing module to carry out scattered radiation correction by determining parameters, characterizing an outer object contour in a scanning plane, from measured data of different x-ray projections, at least one of retrieving an assigned scattered radiation distribution from a database and interpolating a scattered radiation distribution from scattered radiation distributions for object contour sections with similar characterizing parameters, for each x-ray projection, on the basis of at least one object contour section whose characterizing parameters are determined from x-ray projections that lie at least one of in front of and behind the respective x-ray projection by a defined projection angle range, and using the at least one of retrieved and interpolated scattered radiation distribution for correction of the measured data of a respective x-ray projection.

15. A computer readable medium including program segments for, when executed on a computer device, causing the computer device to implement the method of claim 1.

16. An x-ray imaging system, comprising:

a plurality of x-ray sources, movable around an examination object in at least one scanning plane during a measurement pass;

at least one x-ray detector to record, during the measurement pass, a number of x-ray projections at different projection angles with simultaneous use of the x-ray sources;

means for determining parameters, characterizing an outer object contour in a scanning plane, from measured data of different x-ray projections;

means for at least one of retrieving an assigned scattered radiation distribution from a database and interpolating a scattered radiation distribution from scattered radiation distributions for object contour sections with similar characterizing parameters, for each x-ray projection, on the basis of at least one object contour section whose characterizing parameters are determined from x-ray projections that lie at least one of in front of and behind the respective x-ray projection by a defined projection angle range; and means for using the at least one of retrieved and interpolated scattered radiation distribution for correction of the measured data of a respective x-ray projection.

* * * * *